(12) United States Patent
McNair

(10) Patent No.: US 10,671,703 B1
(45) Date of Patent: Jun. 2, 2020

(54) MAINTAINING STABILITY OF HEALTH SERVICES ENTITIES TREATING INFLUENZA

(71) Applicant: Cerner Innovation, Inc., Kansas City, KS (US)

(72) Inventor: Douglas S. McNair, Leawood, KS (US)

(73) Assignee: Cerner Innovation, Inc., Kansas City, KS (US)

(\*) Notice: Subject to any disclaimer, the term of this patent is extended or adjusted under 35 U.S.C. 154(b) by 896 days.

(21) Appl. No.: 15/083,090

(22) Filed: Mar. 28, 2016

Related U.S. Application Data

(60) Provisional application No. 62/138,523, filed on Mar. 26, 2015.

(51) Int. Cl.
*G06F 19/00* (2018.01)
*G16H 50/50* (2018.01)
*G16H 50/80* (2018.01)

(52) U.S. Cl.
CPC ........... *G06F 19/328* (2013.01); *G16H 50/50* (2018.01); *G16H 50/80* (2018.01)

(58) Field of Classification Search
CPC ....... G06F 19/328; G16H 50/50; G16H 50/80
See application file for complete search history.

(56) References Cited

U.S. PATENT DOCUMENTS

| | | | |
|---|---|---|---|
| 6,321,212 B1 | 11/2001 | Lange | |
| 7,711,634 B2 | 5/2010 | Klugman | |
| 8,311,922 B2 | 11/2012 | Coughlan et al. | |
| 8,315,937 B1 | 11/2012 | Schoen et al. | |
| 8,321,329 B1 | 11/2012 | Schoen et al. | |
| 8,527,388 B1 | 9/2013 | Schoen et al. | |
| 8,577,777 B1 | 11/2013 | Schoen et al. | |
| 8,805,704 B2 | 8/2014 | Lewis et al. | |
| 2007/0185742 A1 | 8/2007 | Chapin et al. | |
| 2011/0264601 A1 | 10/2011 | Deng | |

OTHER PUBLICATIONS

Barrieu, et al, "The Handbook of Insurance-Linked Securities," Wiley, 2009, (Hard Cover Book being dated Feb. 22, 2017), 372 pp.

*Primary Examiner* — Eliza A Lam

(74) *Attorney, Agent, or Firm* — Shook, Hardy & Bacon L.L.P.

(57) ABSTRACT

Systems, methods and computer-readable media are provided for determining and mitigating the aggregate loss risk associated with hospitalization for epidemic or pandemic influenza for health insurers, reinsurers, provider organizations, or public policy-makers. An accurate prediction of this risk may be provided, which may be used to determine parameters for reinsurance underwriting or for issuance and trading of catastrophe bonds ("cat bonds") or other insurance-linked securities (ILS) and derivatives to lay off substantial amounts of such risk to capital markets investors. In particular, one embodiment uses a novel log-expit transformation of the raw data and non-parametric gradient-boosting machine-learning modeling in order to determine a high-claim right-tail risk. Some embodiments further comprise securitizing epidemic or pandemic influenza acute care health services catastrophe risk.

20 Claims, 11 Drawing Sheets

$$expit(f(\beta_0, \beta_1 x_1, \ldots, \beta_n x_n)) = \frac{e^{f(\beta_0, \beta_1 x_1, \ldots, \beta_n x_n)}}{(1 + e^{f(\beta_0, \beta_1 x_1, \ldots, \beta_n x_n)})}$$

$$logit(p) = expit^{-1}(p) = ln\left[\frac{p}{1-p}\right]$$

FIG. 3.

```
################################################################################

# Tweedie gradient boosting regression of log-expit transformed hospital charges data

########################################################################## library(TDboost)
library(rje)
library(extRemes)
library(fitdistrplus)
library(evd)
library(ghyp)

# load dataset on which to train model 2007-13 flu seasons admissions
# los,teach,amivir,month,quarter,exp,medi,bedlt200,south,age_dec,female,charge
data1 <- read.csv(file="c:/0_cerdsm/IP/cat_bonds_flu/2007_13.csv", header=TRUE,
  colClasses=rep("integer",12))
nrow(data1)      # 11,823 check whether conventional extreme value distribution or inverse gaussian distribution adequately fit data
fit.chg1 <- fevd(data1$charge)
fit.chg1 fit.chg2 <- fit.NIGuv(data1$charge, opt.pars=c(alpha.bar=FALSE), alpha.bar=1, control=list(abstol=1e-8))
fit.chg2

# QQ plots to inspect goodness of fit of conventional models to data
plot(fit.chg1)
f.pred <- revd(nrow(data1), loc=1.097e+04, scale=9.384e+03, shape=7.277e-01)
qq1 <- qqplot(data1$charge, f.pred, pch=1, cex=0.8, col="red", lwd=1)

multivariate.ghyp <- ghyp(sigma=9.356e+00, mu=-1.345e+03, gamma=2.812e+04)
f.pred <- rghyp(nrow(data1), multivariate.ghyp)
qq2 <- qqplot(data1$charge, f.pred, pch=1, cex=0.8, col="red", lwd=1)

# load test dataset to be predicted 2013-14 flu season admissions
data2 <- read.csv(file="c:/0_cerdsm/IP/cat_bonds_flu/2013_14.csv", header=TRUE,
  colClasses=rep("integer",12))
nrow(data2)      # 4,318 coeffs for affine transform to remove offset and scale to (0,3) range in expit arg
a0 <- -6.0
a1 <-  2.0 subset data with charges < $1M, log-expit transform it
data1 <- subset(data1, charge < 1e06)
data1 <- subset(data1, charge >= 1e03)
data1$charge <- log10(data1$charge)
data1$charge <- expit(a1*data1$charge + a0)
length(data1$charge) # 11,823

.
           .
           .
```

CONTINUES IN FIG. 6B

*FIG. 6A.*

CONTINUES FROM FIG. 6A

```
data2 <- subset(data2, charge < 1e06)
data2 <- subset(data2, charge >= 1e03)
data2$charge <- log10(data2$charge)
data2$charge <- expit(a1*data2$charge + a0)
length(data2$charge) # 4,318 training on data1, 10000 iterations, all vars are continuous numeric
TDboost1 <- TDboost(charge ~ teach + amivir + medi + bedlt200 + south + age_dec,
 data=data1,
 var.monotone=c(0,0,0,0,0,0),        # -1: monotone decrease, +1: monotone increase, 0: no monotone
restrictions
 distribution=list(name="EDM",alpha=1.5), # specify Tweedie index parameter in range (1,2) exclusive
 n.trees=10000,              # number of trees
 shrinkage=0.005,              # shrinkage or learning rate, 0.001 to 0.1 usually work
 interaction.depth=3,           # 1: additive model, 2: two-way interactions, etc.
 bag.fraction=0.5,            # subsampling fraction, 0.5 is probably best
 train.fraction=0.5,           # fraction of data for training, first train.fraction*N used for training
 n.minobsinnode=10,             # minimum total weight needed in each node
 cv.folds=10,              # do 10-fold cross-validation
 keep.data=TRUE,              # keep a copy of the dataset with the object
 verbose=TRUE)              # display progress determine optimal iteration number M
best.iter <- TDboost.perf(TDboost1, method="test")
print(best.iter)

# check performance using 10-fold cross-validation
best.iter <- TDboost.perf(TDboost1, method="cv")
print(best.iter)

# plot the performance and variable influence
summary(TDboost1,n.trees=best.iter)     # based on the estimated best number of trees
#      var  rel.inf
# age_dec    51.29
#   teach    19.89
# bedlt200   15.11
#   south     6.96
#    medi     3.60
amivir    3.15 make prediction on data2
f.pred <- predict.TDboost(TDboost1, data2, best.iter)

# QQ plot
qq <- qqplot(data2$charge, f.pred, pch=1, cex=0.8, col="red", lwd=1)

b0 <- -6*qq$regression$coefficients[1]/qq$regression$coefficients[2]
print(paste0("qq b0: ",b0))
b1 <- 6/qq$regression$coefficients[2]
print(paste0("qq b1: ",b1))

# invert the log-expit transform for a selected quantile
print(paste0("10th pctile, data2: ", round(10^(6*quantile(data2$charge, 0.10)),0)))
print(paste0("99.9th pctile, data2: ", round(10^(6*quantile(data2$charge, 0.999)),0)))
print(paste0("10th pctile, f.predict: ", round(10^(b1*quantile(f.predict, 0.10) + b0),0)))
print(paste0("99.9th pctile, f.predict: ", round(10^(b1*quantile(f.predict, 0.999) + b0),0)))
```

*FIG. 6B.*

CONTINUES IN FIG. 6C

CONTINUES FROM FIG. 6B

```
# create marginal plots
# plot variable 6 (age_dec) after "best" iterations
plot.TDboost(TDboost1, 6, best.iter)

# contour plot of variables 1 and 6 after "best" iterations
# plot.TDboost(TDboost1, c(1,6), best.iter)

# check whether adding mortality variable affects accuracy of model fit and predictions
TDboost2 <- TDboost(charge ~ teach + amivir + medi + bedlt200 + south + age_dec + exp,
  data=data1,
  var.monotone=c(0,0,0,0,0,0,0),        # -1: monotone decrease, +1: monotone increase, 0: no monotone restrictions
  distribution=list(name="EDM",alpha=1.5), # specify Tweedie index parameter in range (1,2) exclusive
  n.trees=10000,              # number of trees
  shrinkage=0.005,             # shrinkage or learning rate, 0.001 to 0.1 usually work
  interaction.depth=3,          # 1: additive model, 2: two-way interactions, etc.
  bag.fraction=0.5,           # subsampling fraction, 0.5 is probably best
  train.fraction=0.5,          # fraction of data for training, first train.fraction*N used for training
  n.minobsinnode=10,            # minimum total weight needed in each node
  cv.folds=10,              # do 10-fold cross-validation
  keep.data=TRUE,             # keep a copy of the dataset with the object
  verbose=TRUE)              # display progress determine optimal iteration number M
best.iter <- TDboost.perf(TDboost2, method="test")
print(best.iter)

# check performance using 10-fold cross-validation
best.iter <- TDboost.perf(TDboost2, method="cv")
print(best.iter) # plot the performance and variable influence
summary(TDboost2,n.trees=best.iter)     # based on the estimated best number of trees
#     var  rel.inf
# age_dec   44.31
#    exp   16.62
#   teach   15.24
# bedlt200   11.52
#   south    5.83
#   medi    3.25
amivir    3.22 make prediction on data2
f.pred <- predict.TDboost(TDboost2, data2, best.iter)

# QQ plot
qqplot(data2$charge, f.pred, pch=1, cex=0.8, col="red", lwd=1)

# create marginal plots
# plot variable 6 (age_dec) after "best" iterations
plot.TDboost(TDboost2, 6, best.iter)

# contour plot of variables 1 and 6 after "best" iterations
# plot.TDboost(TDboost2, c(1,6), best.iter)
```

*FIG. 6C.*

MAINTAINING STABILITY OF HEALTH SERVICES ENTITIES TREATING INFLUENZA

CROSS-REFERENCE TO RELATED APPLICATIONS

This application claims the benefit of U.S. Provisional Application No. 62/138,523, titled "Maintaining Stability of Health Services Entities Treating Influenza," filed Mar. 26, 2015, which is hereby expressly incorporated by reference in its entirety.

INTRODUCTION

Influenza is a contagious respiratory illness with a long history of causing human morbidity and mortality. Despite extensive surveillance of seasonal influenza, its economic costs remain difficult to quantify. Although statistical methods have been proposed for estimating the excess hospitalization rate and mortality rate of influenza, few economic studies have attempted to measure the health insurance losses arising from acute-care hospitalizations resulting from influenza.

Major influenza pandemics tend to occur three to four times each century and have a number of characteristics that differ from intermittent influenza epidemics. By definition a pandemic affects a large number of countries worldwide. A pandemic virus, which infrequently encounters the world human population, results in a large number of hospitalized cases and excess mortality. The novelty and virulence of the pandemic virus also makes prevention and control measures difficult as existing vaccines are not effective and production of new vaccine may take six months or more. Antiviral drugs are in general the only virus-specific intervention during the initial response. Neuraminidase inhibitor medications such as oseltamivir and zanamivir have the advantage of conferring almost immediate protection and their use does not interfere with response to inactivated influenza vaccine.

Although it is well recognized that countries must prepare for the next influenza pandemic, the uncertainty regarding the characteristics of the virus, the populations who will be most seriously affected, and the most cost-effective policies make preparation difficult. The potential losses for health services providers, for health insurers, for reinsurers, and for banks in epidemic and pandemic situations may be catastrophic. Financial ruin for even a modest fraction of these entities would have serious and lasting economic consequences for broader society in the affected countries. In particular, unlike other industries, health services have peculiar concerns and limitations and obligations, such as described further herein, that pose unique challenges for similar for maintaining financial stability.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Embodiments of the invention are directed towards systems and methods for determining and mitigating the aggregate loss risk associated with hospitalization for epidemic or pandemic influenza for health insurers, reinsurers, provider organizations, or public policy-makers. An accurate prediction of this risk may be provided, which may be used to determine parameters for reinsurance underwriting or for issuance and trading of catastrophe bonds ("cat bonds") or other insurance-linked securities (ILS) and derivatives to lay off substantial amounts of such risk to capital markets investors. In particular, one embodiment uses a novel log-expit transformation of the raw data and non-parametric gradient-boosting machine-learning modeling in order to determine a high-claim right-tail risk. Some embodiments further comprise securitizing epidemic or pandemic influenza acute care health services catastrophe risk.

Accordingly, in one aspect a method is provided for distributing instruments representing securitized epidemic or pandemic catastrophe risk, implemented on a computer system at a reinsurer. The method includes receiving, at the reinsurer, a first allotment of first risk instruments of a risk class representing one or more epidemic or pandemic catastrophe risks. The risk class being issuable from the computer system at the reinsurer on a recurring basis, each of the first risk instruments having a first issue date and providing a return on an investment, the amount of the return being reduced upon the occurrence of a realization event for the corresponding represented epidemic or pandemic catastrophe risk. The method also includes distributing from the reinsurer, the first risk instruments of the first allotment to one or more investors, wherein the realization event for a given risk class is defined as an occurrence of an event meeting a predetermined impact threshold, the occurrence of the event meeting the predetermined impact threshold is determined according to an index of physical parameters issued by a neutral party, and the physical parameters are related to but separate from catastrophic loss.

In another aspect, a method is provided for securitizing epidemic or pandemic acute-care health services catastrophe risk. The method comprises determining a forecast model for predicting aggregate loss statistical distributions based on historical insurance claims and electronic health record information for a plurality of hospital admissions over a period of time. The method also comprises determining the aggregate loss with confidence-band or Value at Risk (VaR) bounds on the losses thus determined, and establishing one or more risk classes on the system of the reinsurer, each risk class representing one or more epidemic or pandemic catastrophe risks, each risk class being recurringly issuable from the system of the reinsurer or from a financial exchange as risk instruments providing a return on an investment, the amount of the return for a risk instrument being reduced upon the occurrence of a realization event for the corresponding represented epidemic or pandemic catastrophe risk. The method further includes issuing from the reinsurer, a first collection of risk instruments of a first risk class of the one or more risk classes, wherein the realization event for a given risk class is defined as an occurrence of an event meeting a predetermined impact threshold, the occurrence of the event meeting predetermined impact threshold is determined according to an index of epidemic infection-related parameters issued by a neutral party such as the U.S. Centers for Disease Control (CDC) or the World Health Organization (WHO), and the epidemic infection-related parameters are related to but separate from catastrophic loss.

In another aspect, a method is provided for securitizing epidemic or pandemic acute-care health services catastrophe risk. The method includes determining a time series of viral hospital admissions data and claims resulting from these in-patient care episodes and store said time series on machine-readable media; performing exploratory fitting to EVD, IG, and other skew-kurtotic distributions, and evaluate accuracy of fits in right-tail (QQ plots, confidence bands). The method also includes setting coefficients for affine transform to scale and remove offset of claims, applying log-expit transform to the raw claims data, and partition data into training and test datasets. The method further includes setting or determining: variables' fitting constraints (monotonicity), Tweedie index parameter, learning rate for machine-learning boosting algorithm, maximum interaction depth for gradient boosting, subsampling fraction for bagging generation of boosting tree models, a number M of boosting trees to be generated and evaluated, and a number N cross-validation iterations. The method further includes performing M iterations of Tweedie boosting, determine convergence of gradient boosting model, and determining the best iteration in converged model solution.

In some embodiments, the method further includes determining stability of solution by performing N-fold cross-validation boosting iterations, determining the relative influence of variables retained in Tweedie boosting model, and determining predictions using Tweedie boosting model. Some embodiments further include applying inverse log-expit transform to predicted data to convert back to units of original data, evaluating accuracy of fits in right-tail (QQ plots, confidence bands), and applying the model to establish aggregate risk parameters for insurance-linked security or reinsurance.

BRIEF DESCRIPTION OF THE DRAWINGS

The present invention is described in detail below with reference to the attached drawing figures, wherein:

FIG. 3 depicts one embodiment of transforms utilized for estimating high-claims frequency and severity (e.g., expit) and for back-transforming a model's numeric results to corresponding costs (e.g., logit), in accordance with an embodiment of the invention;

FIG. 6A-6C illustratively provides an example embodiment of a computer program routine for determining a prediction model using Tweedie boosting, in accordance with an embodiment of the invention.

DETAILED DESCRIPTION

Figure 1A:
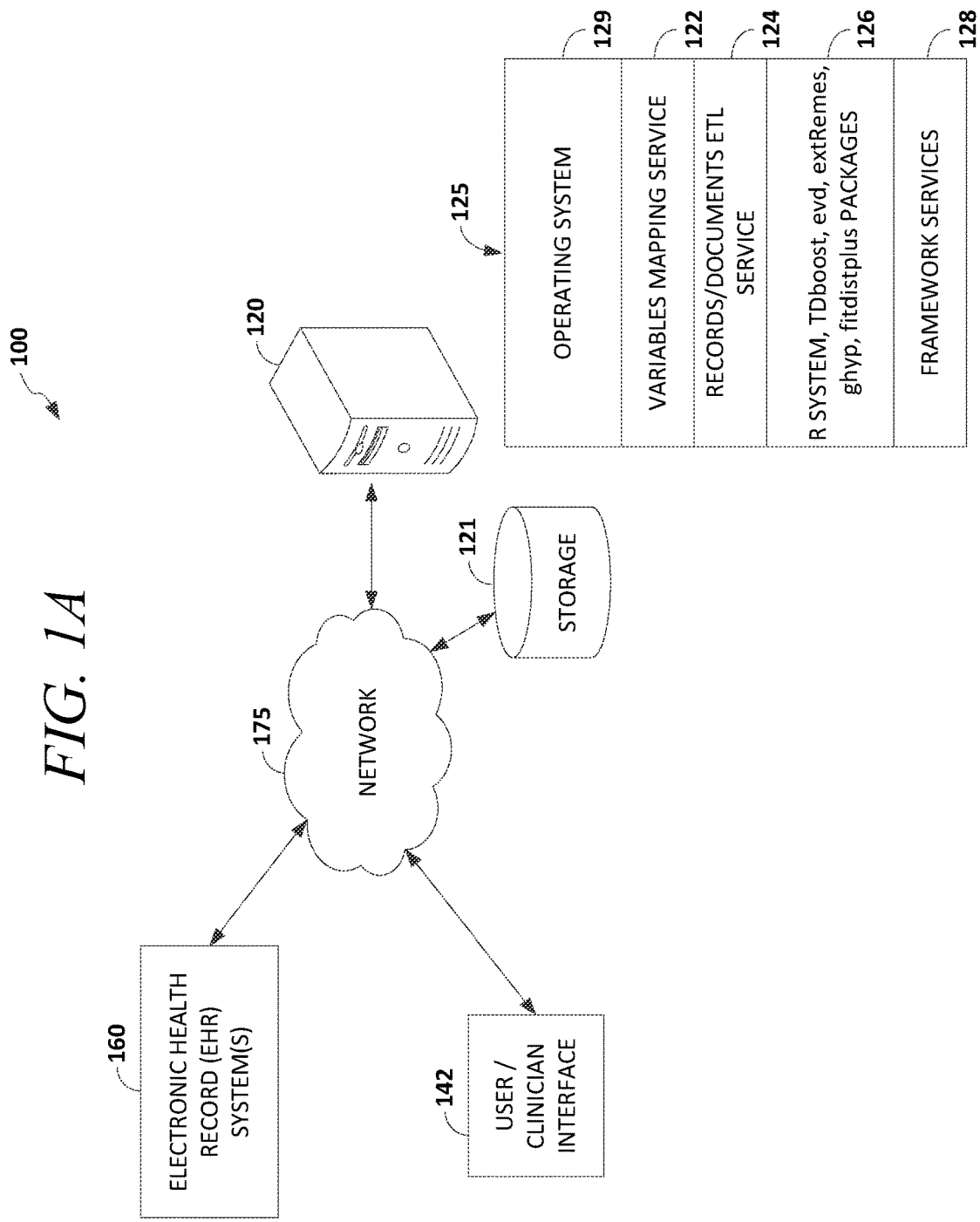
FIGS. 1A and 1B depict aspects of an illustrative architecture suitable for practicing an embodiment of the invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and non-volatile media, removable and nonremovable media, and contemplate media readable by a database, a switch, and various other network devices. By way of example, and not limitation, computer-readable media comprise media implemented in any method or technology for storing information, including computer-storage media (or computer-readable storage devices) and communications media. Examples of stored information include computer-useable instructions, data structures, program modules, and other data representations. Computer storage media or computer-readable storage devices examples include, but are not limited to information-delivery hardware media, RAM, ROM, EEPROM, flash memory or other hardware-based memory technology, CD-ROM, digital versatile discs (DVD), holographic media or other optical disc storage, magnetic cassettes, magnetic tape, magnetic disk storage, other magnetic storage devices, and other computer hardware or hardware storage devices. These technologies can store data momentarily, temporarily, or permanently.

As described previously, Embodiments of the invention provide systems, methods, and computer-readable media for determining and mitigating the aggregate loss risk associated with hospitalization for epidemic or pandemic influenza for health insurers, reinsurers, provider organizations, or public policy-makers. An accurate prediction of this risk may be provided, which may be used to determine parameters for reinsurance underwriting or for issuance and trading of catastrophe bonds ("cat bonds") or other insurance-linked securities (ILS) and derivatives to lay off substantial amounts of such risk to capital markets investors. In particular, one embodiment uses a novel log-expit transformation of the raw data and non-parametric gradient-boosting machine-learning modeling in order to determine a high-claim right-tail risk.

Thus, embodiments of the invention enables reliable estimation of aggregate loss risk across one or more years' time for health insurers, reinsurers, provider organizations, banks, or public policy-makers. The actuarial pricing and reserving of health services-contingent insurance and reinsurance cover involves the calculation of statistics regarding occurrences and amounts of future cash flows. For example, the insurance 'pure premium' (also known as 'benefit premium') can be regarded as the expected value of the prospective benefits cash flow distribution, valued at time zero for a given interest rate structure. The probabilities of the prospective benefits cash flow are based on the occurrence of the policyholder's health events (health contingencies, including admission to hospital). In addition, the theory of interest is used to determine the present value of these amounts that will occur in the future. Therefore, health insurance actuarial mathematics is based on concepts derived from demography and theory of interest.

Contingencies that arise in the context of epidemics or pandemics, such as influenza epidemics, present particular and unique financial challenges to organizations responsible for providing acute health services and providing insurance or reinsurance cover for them. If an epidemic is sufficiently widespread and severe, there will be numerous costly hospitalizations for which reimbursements or insurance or reinsurance paid-in premia for cover in-force will be insufficient. The magnitude of epidemic-related acute-care losses may be so large as to be financially catastrophic to the organizations exposed to such risks.

In other types of economically important catastrophes, such as earthquakes and tropical storms, catastrophe bonds ('cat bonds') often are issued to cover the so-called high layers of reinsurance protection. For example, protection against events that have a probability of occurrence of 2% or less in any given year (that is, a return period of at least 50 years) are frequently the subject of cat bond issuance. The higher layers of protection often go unreinsured by ceding companies for two primary reasons: (a) for events of this magnitude, ceding insurers are concerned about the credit risk of the reinsurer, and (b) high layers tend to have the unaffordably-high reinsurance margins or pricing spreads above the expected loss. The latter reason (b) is particularly true for events whose return period (frequency) and/or severity are regarded as difficult to predict accurately. In such cases, the issuer and investors expect a much higher spread to compensate for the uncertainty in the risk that they are taking, which makes the cover financially unattractive to most sponsors. Alternatively, potential issuers and investors decline to enter into such markets at all, on account of the uncertainty and model risk.

Because cat bonds are fully collateralized, they eliminate concerns about credit risk. This is a significant advantage to sponsors and guarantors and substantially addresses issue (a) above. And because catastrophic events have low correlations with investment returns, cat bonds may provide lower spreads than high-layer reinsurance because they are attractive to a variety of investors for diversification of their portfolios. Cat bonds are more transparent than many other types of asset-backed securities (ABS), such as mortgage-backed securities. Because the payoff on the bonds comes from the assets held in trust, the cat bond sponsor retains a strong interest in the quality of the revenue streams or other assets backing the bond. Therefore, there is less moral hazard with cat bonds than with other types of ABS. As a result of these features, cat bonds weathered the 2008 recession much more successfully than other types of ABS.

An additional advantage is that cat bonds can lock in multi-year cover unlike traditional reinsurance, which usually is written for a one-year period. Cat bonds and other ILS securities can in this way shelter the sponsor from cyclical price fluctuations in the reinsurance market or the evolving willingness of reinsurers to write cover on a year-to-year basis. The multi-year terms (generally, 3-year tenors) of most cat bonds also allow sponsors to spread the fixed costs of issuing the bonds over a multi-year period, reducing the costs on an annualized basis.

While several catastrophe bonds have been issued for hedging life insurers' (and reinsurers') exposure to pandemic mortality risk, no comparable catastrophe bond issuance has to-date been undertaken to hedge health insurers' and reinsurers' exposure to pandemic morbidity-related acute-care health services risk. Largely, this has to do with two factors: (a) the lack of sufficient data of the detailed types necessary for accurate predictive modeling, beyond claims data, and (b) the lack of adequate systems and methods for accurately determining the aggregate risk, especially the risk that is associated with extreme-valued, right-tail high-severity claims.

Referring now to the drawings in general, and initially to FIG. 1A in particular, an aspect of an operating architecture 100 is provided suitable for practicing an embodiment of our invention. We show certain items in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

Operating architecture 100 is one example of a suitable architecture for implementing an embodiment of the invention. As described above, some embodiments of the present invention may be implemented as a system, comprising one or more computers and associated network and equipment, upon which a method or computer software application is executed. Accordingly, aspects of the present invention may take the form of an embodiment combining software and hardware aspects that may all generally be referred to herein as a "module" or "system." Further, the methods of the present invention may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for steps of the methods of the present invention may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

As shown in FIG. 1A, example operating architecture 100 provides an aspect of a computerized system for compiling and/or running embodiments of a system determining and mitigating the aggregate loss risk associated with hospitalization for epidemic or pandemic influenza, such as by securitizing epidemic or pandemic acute-care health services catastrophe risk. Architecture 100 includes one or more electronic health record (EHR) systems, such as hospital EHR system 160, communicatively coupled to network 175, which is communicatively coupled to computer system 120. In some embodiments, components of operating environment 101 that are shown as distinct components may be embodied as part of or within other components of environment 100. For example, EHR systems 160 may comprise one or a plurality of EHR systems such as hospital EHR systems; health information exchange EHR systems; ambulatory clinic EHR systems; psychiatry/neurology EHR systems; insurance, collections or claims records systems; and may be implemented in computer system 120. Similarly, EHR system 160 may perform functions for two or more of the EHR systems (not shown). In an embodiment, EHR system 160 includes historical claims data for health services, apportionment data, and related health services financial data that may be used to determine prices and volumes for health services purchased, sold, and/or delivered.

In embodiments, network 175 includes the Internet, and/or one or more public networks, private networks, other communications networks such as a cellular network, or similar network(s) for facilitating communication among devices connected through the network. Network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system 160 include one or more data stores of health records or health-services related records, which may be stored on storage 121, and may further include one or more computers or servers that facilitate the storing and retrieval of the health records. In some embodiments, EHR system 160 may be implemented as a cloud-based platform or may be distributed across multiple physical locations. EHR system 160 may further include record systems, which store real-time or near real-time patient (or user) information, such as wearable, bedside, or in-home patient monitors, for example.

Example operating environment 100 further includes provider user/clinician interface 142 communicatively coupled to network 175. Embodiments of interface 142 may take the form of a user-clinician interface operated by a software application or set of applications on a client computing device such as a personal computer, laptop, smartphone, or tablet computing device. In one embodiment, the application includes the PowerChart® software, manufactured by Cerner Corporation. In an embodiment, the application is a Web-based application or applet. A provider clinician application facilitates accessing and receiving information from a user or health care provider about a specific patient or population of patients including patient history, health care resource data, claims data, health services financial data, or other health-related information. Interface 142 may be used in the method described in connection to FIG. 2, in some embodiments. Additionally, in some embodiments interface 142 also facilitates receiving orders for the patient from the clinician/user, based on the results. In some embodiments, interface 142 may also be used for providing diagnostic services.

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interfaces 140 and 142. In some embodiments, interface 142 operates in conjunction with software stack 125.

In embodiments, variables mapping (or indexing) service 122 and records/documents ETL service 124 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke software services 126.

Software services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including for example, R packages 'TDboost, 'evd', 'extRemes,' 'ghyp', 'fitdisplus,' or similar services. In an embodiment, software services 126 include the services or routines, which may be embodied as one or more software agents, for determining Tweedie gradient boosting regression of log-expit transformed hospital charges data, as the examples illustratively depicted in FIGS. 6A-6C. (One example of logit and expit functions are illustratively provided in FIG. 3.) In some embodiments, software services 126 are associated with framework services 128, which in one embodiment include Apache Hadoop and Hbase framework, or other frameworks operable for providing a distributed file system, and which in some embodiments may facilitate provide access to cloud-based services such as those provided by Cerner Healthe Intent®.

Example operating environment 100 also includes storage 121 or data store 121, which in some embodiments includes patient data for a candidate or target patient (or information for multiple patients); variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
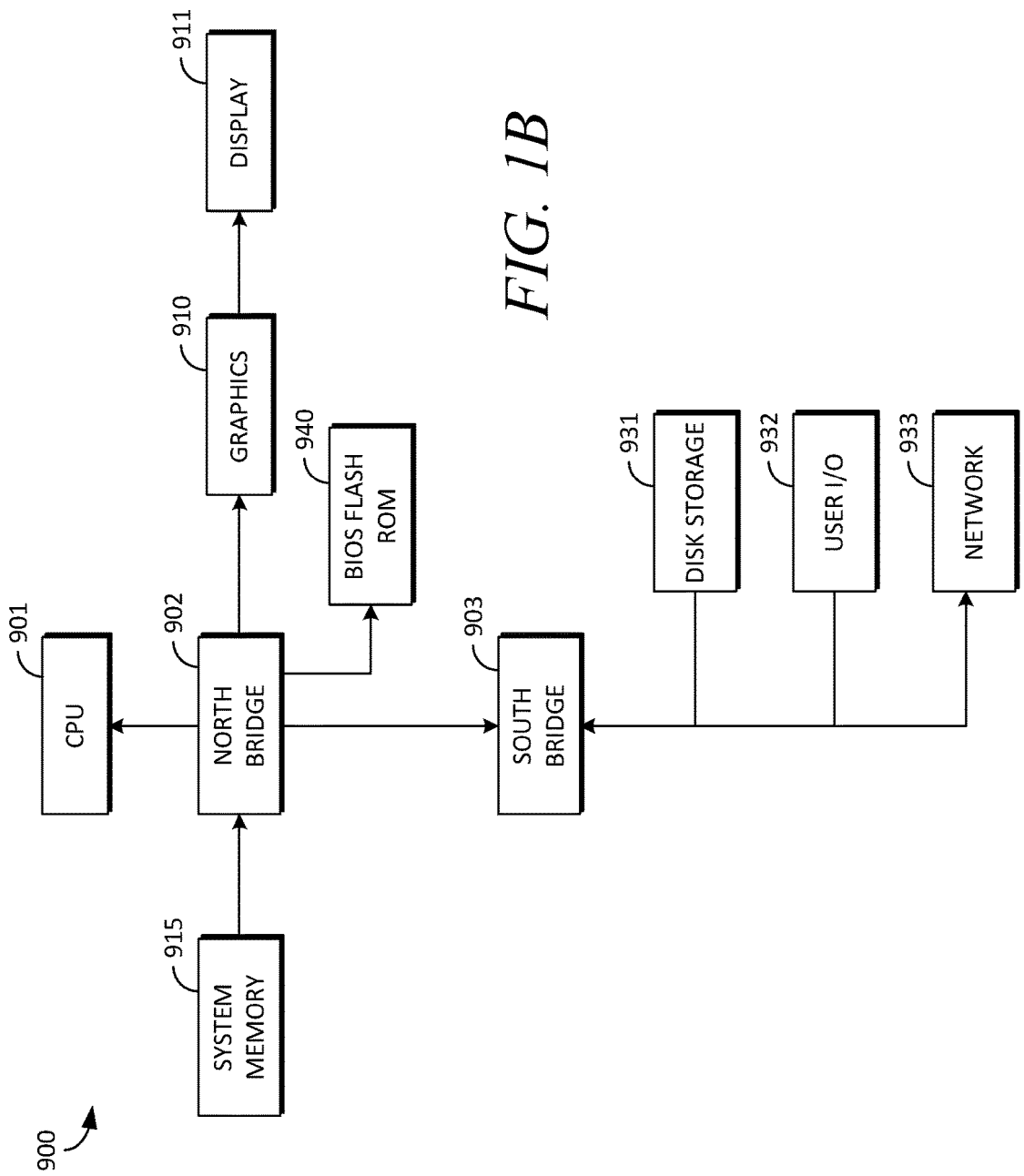

Turning briefly to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

With reference generally to FIG. 2-6C, probabilistic extreme-value theory (EVT) deals with the stochastic behavior of the maximum and the minimum of independent and identically distributed random variables, including the types of data that are associated with acute-care hospital-based health services provisioning. The distributional properties of extremes, as well as of exceedances over (below) high (low) thresholds, are determined by the upper (right) and lower (left) tails of the underlying distribution. In particular, extreme value analysis usually requires estimation of the probability of events that are more extreme than may have been observed. EVT provides a framework that enables this type of extrapolation.

In one aspect, EVT may be considered an approach that comprises methods for model extrapolation based on the implementation of mathematical limits as finite approximations. This suggests an implicit assumption that the underlying stochastic mechanism of the process being modeled is sufficiently smooth to enable extrapolation to as-yet-unobserved levels. In one aspect, because the reinsurance industries have experienced higher losses in recent years from unprecedented catastrophes, extreme value modeling should be an exceptionally useful tool in emergency management, including improvements in reinsurance underwriting and cat bond issuance. However, it is important to recognize the limitations of extreme value modeling. First, models are typically developed using asymptotic assumption, so caution is needed in treating the models as exact results, given that they are produced from finite samples. Second, the models themselves are typically derived under particular circumstances that may or may not prevail in the future, and third, the models may lead to information loss when implemented in practice.

Other approaches to this problem have employed conventional statistical regression models by treating zero outcomes as censored below some cutoff point, but these approaches rely on a normality assumption of the latent response. Alternatively, some efforts have used generalized linear models (GLMs) with a Tweedie-distributed outcome to simultaneously model the frequency and severity of insurance claims. They assume Poisson arrival of claims and gamma-distributed amount for individual claims so that the size of the total claim amount follows a Tweedie compound Poisson distribution. Due to its ability to simultaneously model the zeros and the continuous positive outcomes, Tweedie GLM has been a widely-used method in actuarial studies.

However, despite of the popularity of the Tweedie GLM and related methods, a major limitation is that the link function of such methods is restricted to a linear form, and this linear structure can be inadequate to represent real-world data with sufficient accuracy for purposes such as cat bond pricing. Although nonlinearity may alternatively be modeled by adding splines, low-degree splines are likewise inadequate to capture the non-linearity features that are usually manifested by the data, while high-degree splines often result in 'over-fitting,' which in turn produces unstable estimates and excessive model risk from the point of view of risk underwriters. Yet another alternative, generalized additive models [GAMLSS], overcome the restrictive linear assumption of GLMs, and can model continuous variables by smooth functions estimated from data. The structure of such models, however, has still to be determined a priori. That is, the method entails ad hoc specification of the main effects and interaction effects to be used in the model. As a result, misspecification of non-ignorable effects frequently degrades prediction accuracy. In view of the foregoing, a non-parametric system and method that does not require a priori specification of model structure is much better for the particular and unique challenges arising from catastrophic risks associated with epidemic or pandemic acute-care health services. In summary, the existing approaches have several limitations, including, for example: (1) Omission of basis characteristics that characterize multivariate patterns in the high-claim right-tail of the statistical distribution of losses associated with hospital care in epidemic or pandemic situations; (2) Regression methods that give undue weight to left-tail low-severity claims; (3) Excessive imprecision in right-tail loss predictions; (4) Parametric model structure whose assumptions are violated by the data; (5) Heteroskedasticity in the data that interferes with model convergence; (6) Claims distributions' right- and/or left-truncation or platykurtosis; and (7) Inaccuracy (over- or under-prediction biasing of predicted aggregate losses) due to the foregoing causes. Additionally, the in-hospital mortality rate is, in general, very weakly correlated with claim amount, such that the triggers and systems and methods that have previously been used for pandemic life risk cat bonds are unsuitable for health services (pandemic morbidity) cat bonds.

Accordingly, it is therefore valuable for providing embodiments of the invention described herein that mitigate the aforementioned limitations and providing superior accuracy and precision particularly in the high-claim right tail of the predicted loss distribution, which is key to establishing realistic reinsurance cover or cat bond or other insurance-linked securities hedging.

Figure 2:
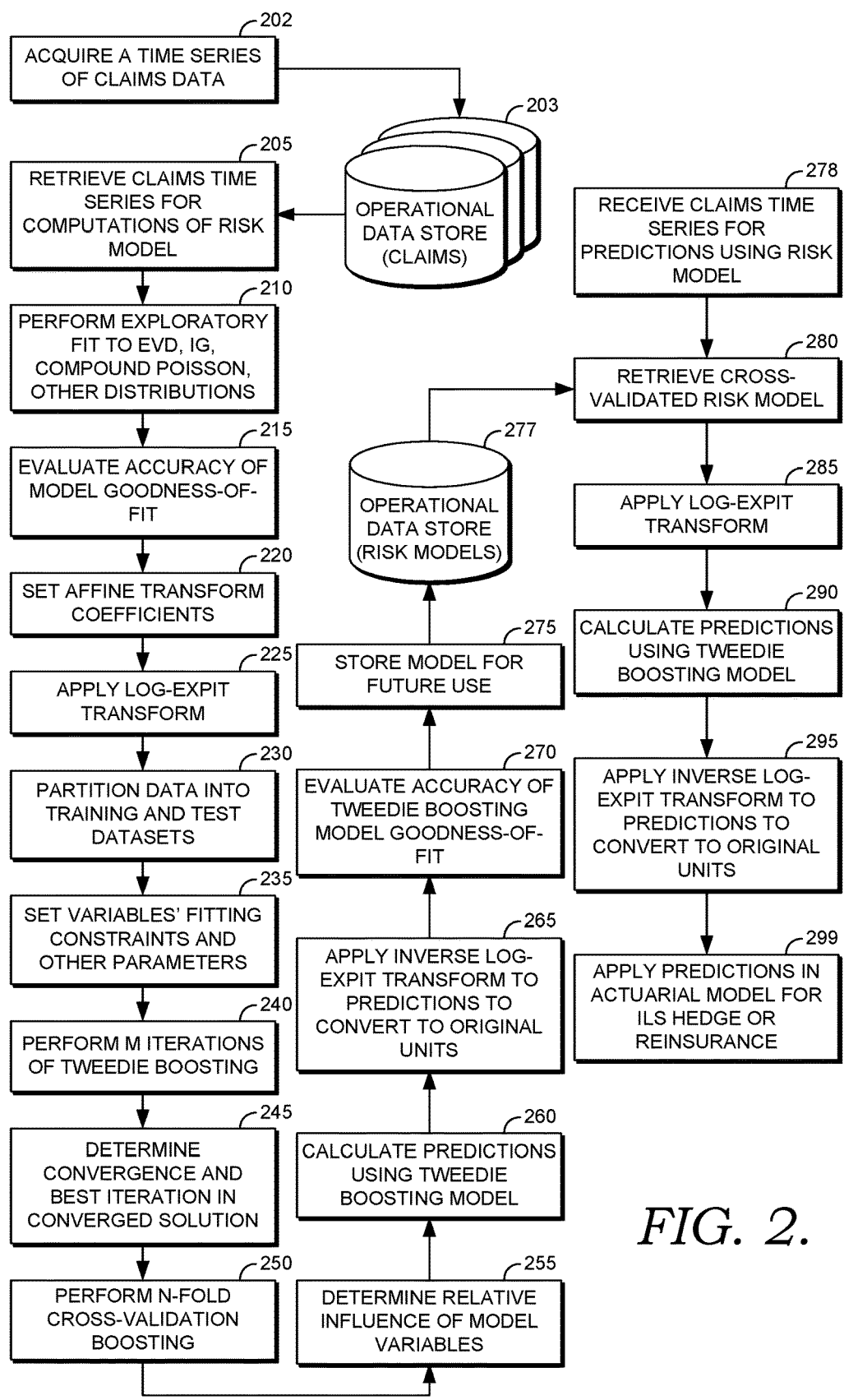
FIG. 2 depicts a flow diagram of an exemplary method for determining aggregate loss risk associated with hospitalization for epidemic or pandemic influenza, in accordance with an embodiment of the invention.
Figure 4A:
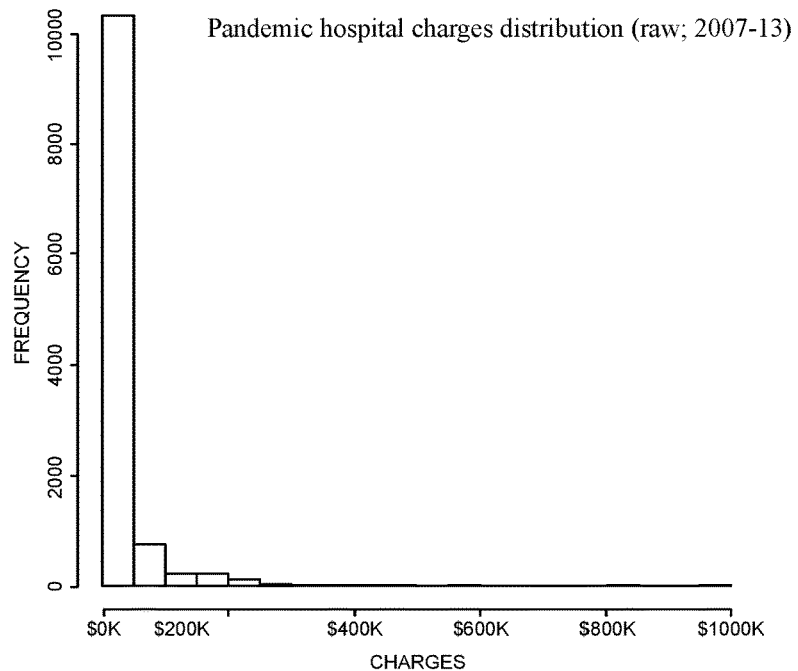
FIGS. 4A and 4B depict an example statistical distribution of charges.
Figure 4B:
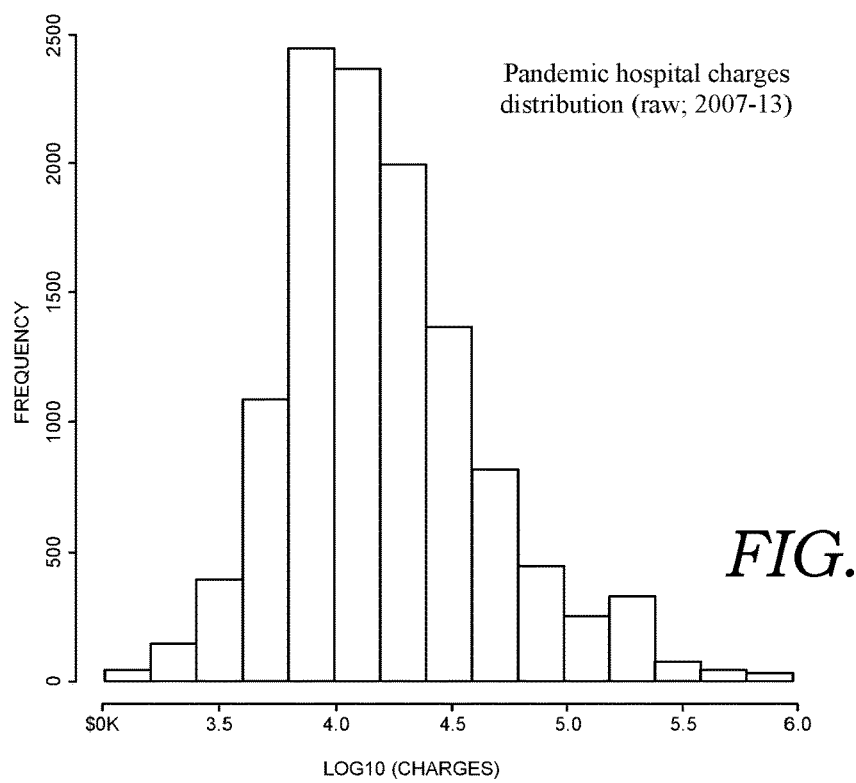
Figure 5A:
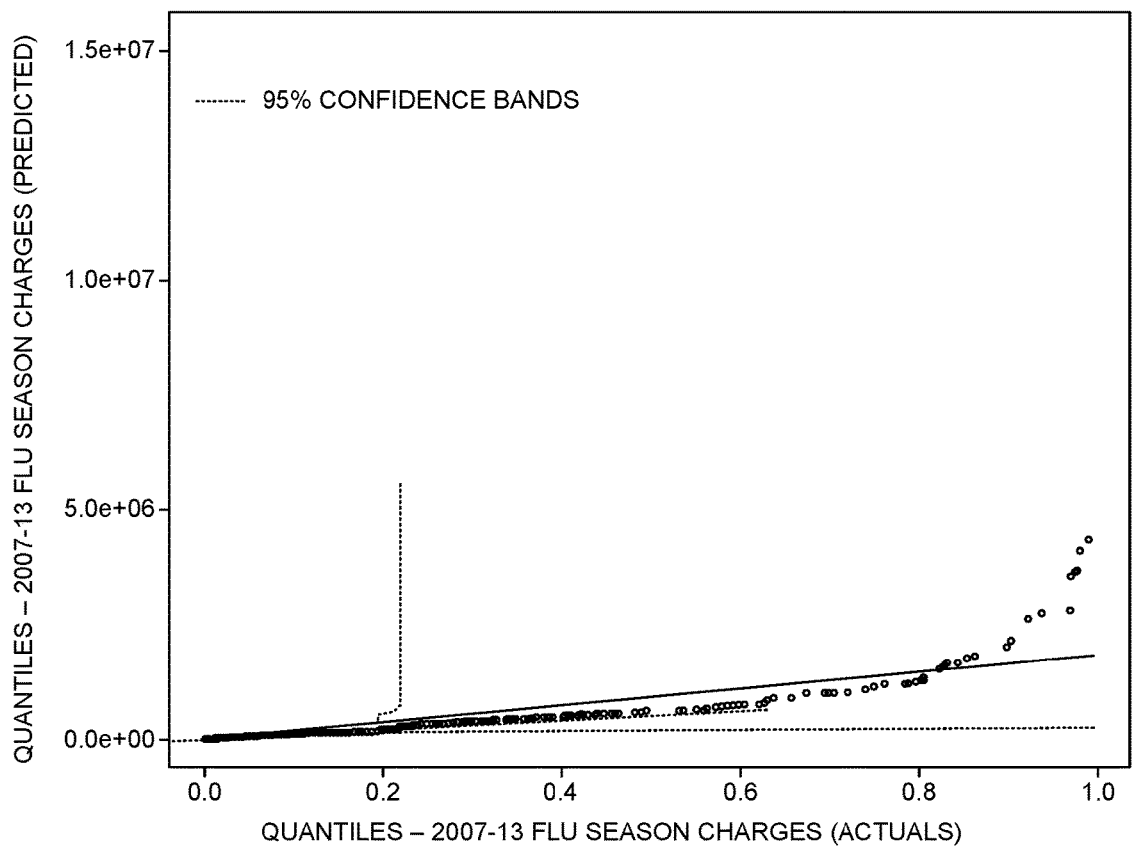
FIGS. 5A-5C depict Quantile-Quantile plots of predicted vs. actual flu season charges.
Figure 5B:
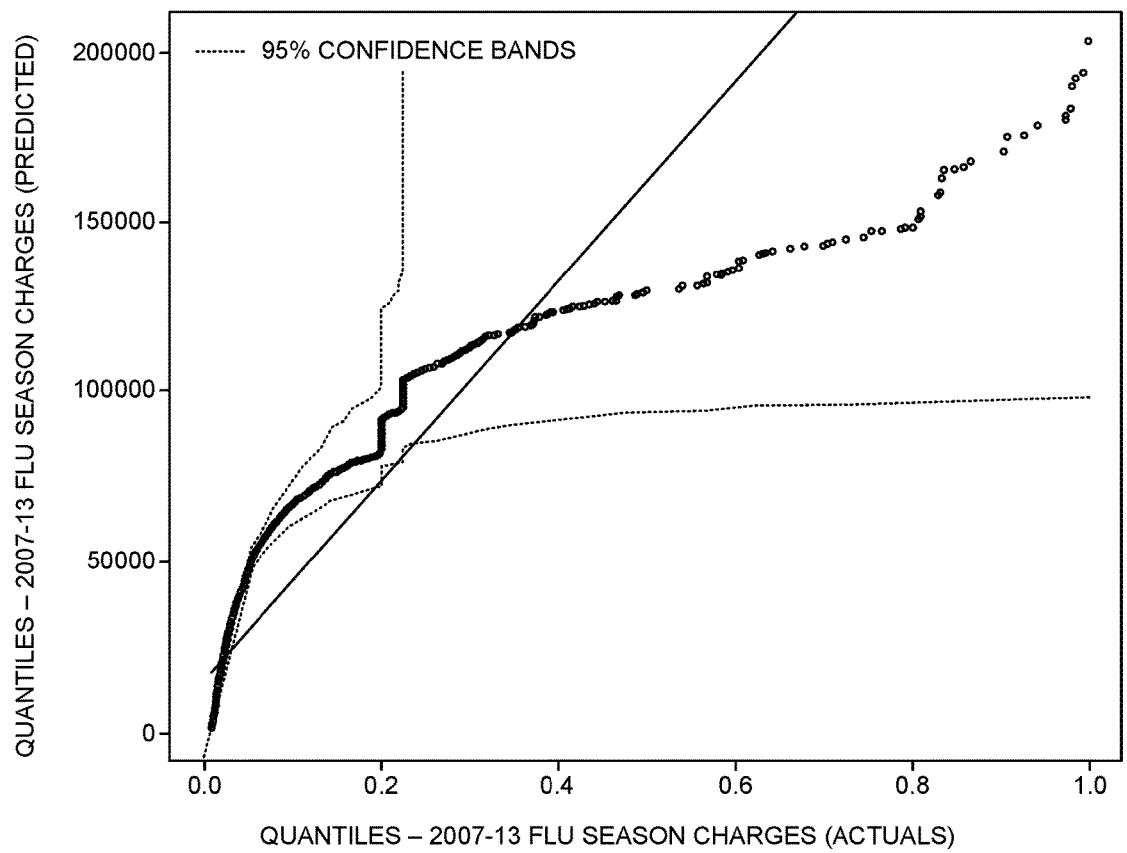
Figure 5C:
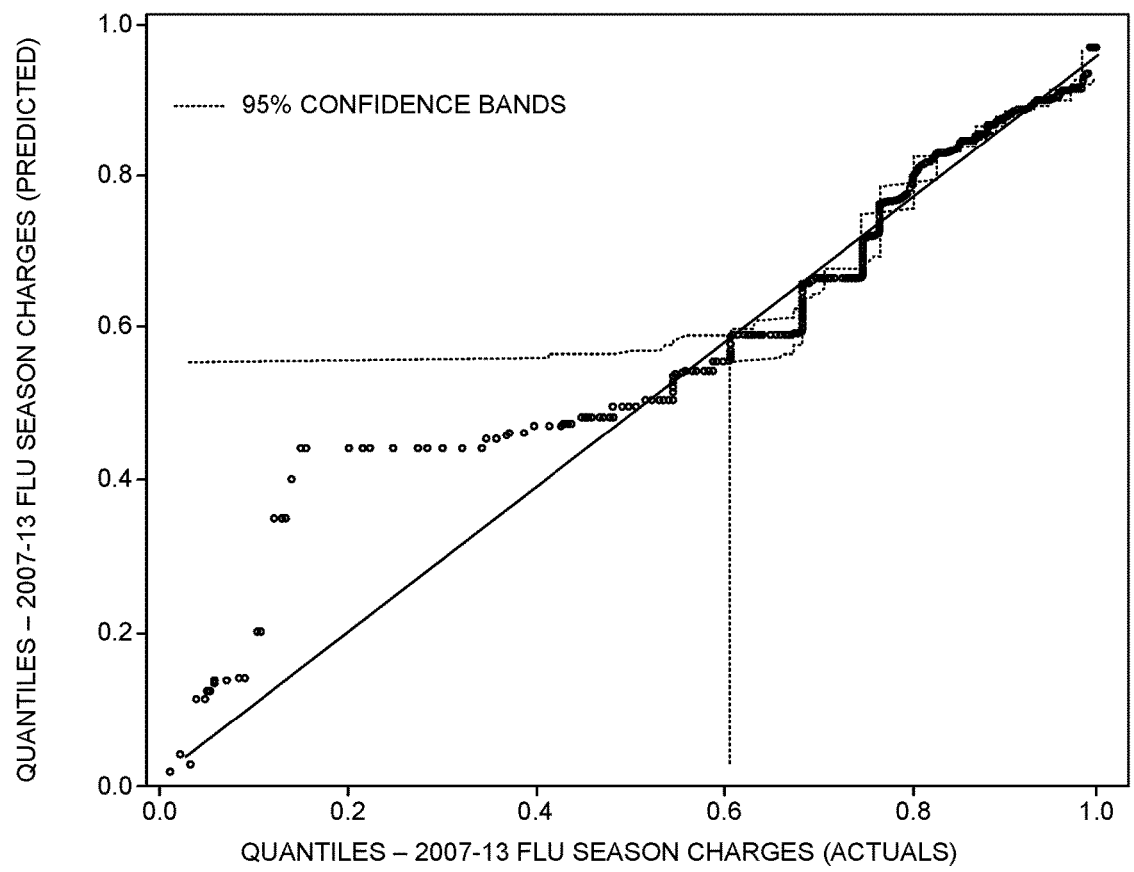

Turning to FIG. 2, a portion of a data and process flow (or method) 200 is shown for generating gradient boosting models on the transformed hospital charges data. Method 200 may be used for determining aggregate loss risk associated with hospitalization for epidemic or pandemic influenza, for use in some embodiments of the invention, and described herein. In one embodiment, method 200 may be facilitated using the example computer program provided in FIGS. 6A-6C.

Accordingly, at a step 202, time series data is acquired of viral hospital admissions data and claims resulting from these in-patient care episodes and store said time series on machine-readable media. At step 205, receive this time series data, which may be accessed from operational data store 203, (which may be embodied as EHR 160 and/or storage 121 or FIG. 1A). At step 210, exploratory fitting to EVD, IG, and other skew-kurtotic distributions is performed. At step 215, the accuracy of fits in right-tail is evaluated. For example, in an embodiment, this includes Quantile-Quantile (QQ) plots and/or confidence bands. Examples of QQ plots are illustratively provided in FIGS. 5A-5C. At step 220, determine coefficients for affine transform to scale and remove offset of claims. In an embodiment, these coefficients are set and may be based on pre-defined values, rules, or logic. At step 225, log-expit transform is applied to the raw claims data. Examples of an embodiment of logit and expit transformations are illustratively provided in FIG. 3. At step 230, the data is partitioned into training and test datasets. At step 235, set variables' fitting constraints (e.g., monotonicity), and other parameters. In some embodiments step 235 comprises setting (or determining) one or more of the Tweedie index parameter, a learning rate for machine-learning boosting algorithm, a maximum interaction depth for gradient boosting, a subsampling fraction for bagging generation of boosting tree models, a number M of boosting trees to be generated and evaluated, and a number N cross-validation iterations. Examples of these parameters are provided in the example computer program shown in FIG. 6A-6C.

At step 240, perform M iterations of Tweedie boosting, where m is determined from step 235. At step 245, determine convergence of gradient boosting model and best iteration in converged model solution. At step 250, determine stability of solution by performing N-fold cross-validation boosting iterations. At step 255, determine the relative influence of variables retained in Tweedie boosting model. At step 260, calculate predictions using Tweedie boosting model. At step 265, apply inverse log-expit transform to predicted data to convert back to units of original data.

At step 270, the accuracy of fits in right-tail (e.g., QQ plots, confidence bands) is evaluated. At step 275, the trained model may be stored (e.g., in operational data store 277, which may be embodied as storage 121 of FIG. 1A) for future use. At step 278, a claims time series is received for prediction using the risk model(s) stored in data store 2777. At step 280, the risk model(s) are retrieved. At step 285, apply the log-expit transform to the claims data received in step 278. At step 290, calculate predictions using the Tweedie boosting model. At step 295, apply inverse log-expit transform to the predictions to convert them to their original units. And at step 299, apply the model to establish aggregate risk parameters for insurance-linked security or reinsurance. In an embodiment, the predictions may be applied in an actuarial model for ILS hedge or reinsurance.

With reference now to FIGS. 1A-6C, an example embodiment was reduced to practice using a computer running the Linux operating system, the open-source statistical software package R, and the R modules TDboost, evd, extRemes, ghyp, and fitdistrplus. In this embodiment, an illustrative time series of claims data was retrieved, consisting of de-identified, privacy-protected, secondary-use-permitted HIPAA-compliant records for 6 influenza seasons (2007-2013), where each flu season begins in week 40 of a calendar year and concludes at the end of week 39 the following year, as is customary for U.S. Centers for Disease Control and other national health agencies. The records comprised electronic health records and claims information for 18,422 distinct individuals' in-patient hospital stays in 616 U.S. hospitals that participate in Cerner Health Facts® data warehouse. These 6 seasons' data were utilized for determining mathematical models representing claims experience and for back-testing the models. FIGS. 4A and 4B illustrate the distributions of pandemic hospital charges over this time period.

In this example embodiment, compound Tweedie regression was performed via 10,000 iterations of a non-parametric gradient-boosting machine-learning algorithm, followed by 10-fold cross-validation to determine the best iteration and the numerical stability of the model thus produced. Records for a further 4,318 individuals' completed and charged in-patient hospital stays were retrieved for the 2013-2014 influenza season. The best model from the previous steps was applied to the 2013-14 season time series to assess how accurately the model predicted the claims distribution for the 2013-14 season.

While the invention has been described in terms of a single preferred embodiment, those skilled in the art will recognize that the invention can be practiced with modification within the spirit and scope of the appended claims.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention. A number of embodiments are now provided:

Embodiment 1

A method for securitizing epidemic or pandemic acute-care health services catastrophe risk comprising: determining a mathematical model predicting aggregate loss statistical distributions based on historical insurance claims and electronic health record information for a plurality of hospital admissions over a period of time; determining the aggregate loss with confidence-band or Value at Risk (VaR) bounds on the losses thus determined; establishing one or more risk classes on the system of the reinsurer, each risk class representing one or more epidemic or pandemic catastrophe risks, wherein each risk class being recurringly issuable from the system of the reinsurer or from a financial exchange as risk instruments providing a return on an investment, and wherein the amount of the return for a risk instrument being reduced upon the occurrence of a realization event for the corresponding represented epidemic or pandemic catastrophe risk; and issuing a first collection of risk instruments of a first risk class of the one or more risk classes, wherein the realization event for a given risk class is defined as an occurrence of an event meeting a predetermined impact threshold, wherein the occurrence of the event meeting predetermined impact threshold is determined according to an index of epidemic infection-related parameters issued by a neutral party such as the U.S. Centers for Disease Control (CDC) or the World Health Organization (WHO), and the epidemic infection-related parameters are related to but separate from catastrophic loss.

Embodiment 2

The method of embodiment 1, wherein the one or more risk classes include a plurality of risk classes each representing an individual epidemic or pandemic catastrophe risk, and one or more risk classes representing a combination of epidemic or pandemic catastrophe risks represented by two or more of the plurality of risk classes.

Embodiment 3

The method of embodiments 1 or 2, wherein the mathematical modeling includes transforming the raw claims data by a transform such as a log-expit function, whose effect is to place emphasis on the high-value right-tail of the claims distribution during model generation and a non-parametric machine-learning method to determine a mathematical model from said transformed claims data.

Embodiment 4

The method of any of embodiments 1 to 3, wherein issuing the first collection of risk instruments includes issuing the first collection of risk instruments on a first issue date the method further comprising: issuing a second collection of risk instruments of the first risk class on a second issue date, the second issue date being after the first issue date.

Embodiment 5

The method of any of embodiments 1 to 4, wherein the risk instruments of the first risk class have an associated plurality of terms, the plurality of terms including class terms and series terms, the class terms being defined for all risk instruments of the first risk class during the establishing of the first risk class, the series terms being defined for risk instruments of a given collection of risk instruments of the first series at the time of issuance of the collection, the series terms including an interest spread defining an amount payable to an investor, and a maturity date defining a date on which a principal amount will be returned to the investor if no realization event has occurred.

Embodiment 6

The method of any of embodiments 1 to 5, wherein the risk classes represent epidemic or pandemic catastrophe risks selected from the group consisting of influenza, respiratory syncytial virus, and bacterial pneumonias that may frequently be sequelae of primary viral respiratory infection.

Embodiment 7

The method of any of embodiments 1 to 6, wherein the risk classes categorize epidemic or pandemic catastrophe risks by region or by time period.

Embodiment 8

The method of any of embodiments 1-7 wherein the model includes cumulative in-patient charges arising from influenza admissions per 1,000 admissions to hospital as a function of one or more variables such as the season-to-date's mechanical ventilation procedure rate (ICD-9 procedures 96.7), acute dialysis procedure rate (ICD-9 procedures 54.98 or 38.95), rate of discharge to SNF or LTAC facilities, or in-hospital mortality rate.

Embodiment 9

The method of any of embodiments 1-8 wherein the hospital-related information includes one or more variables such as bed-size, teaching status, and geographic location (GIS coordinates).

Embodiment 10

The method of any of embodiments 1-9 wherein the region- or community-related information includes one or more variables such as vaccine uptake rate, timing of vaccine availability, spectrum of vaccine effectiveness against the virus strains that are prevalent in each time period.

Embodiment 11

A method of distributing instruments representing securitized epidemic or pandemic catastrophe risk, the method comprising: receiving, at the computer system of the reinsurer, a first allotment of first risk instruments of a risk class representing one or more epidemic or pandemic catastrophe risks, the risk class being issuable from the computer system at the reinsurer on a recurring basis, each of the first risk instruments having a first issue date and providing a return on an investment, the amount of the return being reduced upon the occurrence of a realization event for the corresponding represented epidemic or pandemic catastrophe risk; and distributing the first risk instruments of the first allotment to one or more investors, wherein the realization event for a given risk class is defined as an occurrence of an event meeting a predetermined impact threshold, the occurrence of the event meeting the predetermined impact threshold is determined according to an index of physical parameters issued by a neutral party, and said physical parameters are related to but separate from catastrophic loss.

Embodiment 12

The method of embodiment 11, further comprising: receiving an allotment of second risk instruments of the risk class representing the one or more epidemic or pandemic catastrophe risks, each of the second risk instruments having a second issue date, the second issue date being after the first issue date; and distributing the second risk instruments of the second allotment to the one or more investors.

Embodiment 13

The method of embodiments 11 or 12, wherein the risk instruments of the risk class have an associated plurality of terms, the plurality of terms including class terms and series terms, the class terms being defined for all risk instruments of the risk class, the series terms being defined for risk instruments of a given collection of risk instruments of the first series at the time of issuance of the collection, the series terms including an interest spread defining an amount payable to an investor, and a maturity date defining a date on which a principal amount will be returned to the investor if no realization event has occurred.

Embodiment 14

A method of securitizing epidemic or pandemic catastrophe risk, comprising: establishing one or more risk classes, each risk class representing one or more epidemic or pandemic catastrophe risks, each risk class being recurringly issuable as risk instruments providing a return on an investment, the amount of the return for a risk instrument being reduced upon the occurrence of a realization event for the corresponding represented epidemic or pandemic catastrophe risk; and issuing a first collection of risk instruments of a first risk class of the one or more risk classes, wherein the realization event for a given risk class is defined as an occurrence of an event meeting a predetermined impact threshold, and the occurrence of the event meeting the predetermined impact threshold is determined according to an index of physical parameters issued by a neutral party, and said physical parameters are related to but separate from catastrophic loss.

Embodiment 15

The method of embodiment 14, wherein the one or more risk classes include a plurality of risk classes each representing an individual epidemic or pandemic catastrophe risk, and one or more risk classes representing a combination of epidemic or pandemic catastrophe risks represented by two or more of the plurality of risk classes.

Embodiment 16

The method of embodiments 14 or 15, wherein the individual epidemic or pandemic catastrophe risks are uncorrelated or only weakly correlated by time interval or across regions.

Embodiment 17

The method of any of embodiments 14-16 wherein the computer program instructions cause the computer to execute the method further comprising: issuing the first collection of risk instruments on a first issue date; and issuing a second collection of risk instruments of the first risk class on a second issue date, the second issue date being after the first issue date.

Embodiment 18

The method of any of embodiments 14-17 wherein the risk instruments of the first risk class have an associated plurality of terms, the plurality of terms including class terms and series terms, the class terms being defined for all risk instruments of the first risk class during the establishing of the first risk class, the series terms being defined for risk instruments of a given collection of risk instruments of the first series at the time of issuance of the collection, the series terms including an interest spread defining an amount payable to an investor, and a maturity date defining a date on which a principal amount will be returned to the investor if no realization event has occurred.

Embodiment 19

The method of any of embodiments 14-18 wherein the risk classes represent epidemic or pandemic catastrophe risks selected from the group consisting of in-patient acute-care hospital care, long-term acute care (LTAC), or skilled nursing facility (SNF) care.

Embodiment 20

The method of any of embodiments 14-19 wherein the risk classes categorize epidemic or pandemic catastrophe risks by region or by time period.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A method for securitizing epidemic or pandemic acute-care health services catastrophe risk comprising:
   receiving structured data comprising non-classified historical insurance claims and electronic health record information for a plurality of hospital admissions over a duration of time from a network-based non-transitory storage device;
   generating a set of transformed data using one or more processors executing instructions that cause one or more processors to perform an expit transformation on the received structured data;
   generating one or more risk classification instruments using a model developed to predict aggregate risk based on a distribution of the set of transformed data;
   establishing a communication coupling with a networked server accessible by multiple users; and
   publishing a first collection of the one or more risk classification instruments to the server.

2. The method of claim 1, wherein each of the one or more risk classification instruments represent an individual epidemic or pandemic catastrophe determined by the model based on a diagnosis included in the electronic health record information.

3. The method of claim 1, wherein the model includes machine-learning trained with classified historical insurance claims and corresponding electronic health record information.

4. The method of claim 1, wherein issuing the first collection of the one or more risk classification instruments corresponds to a first issue date, and wherein the method further comprises issuing a second collection of risk instruments of the one or more risk classification instruments on a second issue date, the second issue date being after the first issue date.

5. The method of claim 4, wherein the one or more risk classification instruments have an associated plurality of terms, the plurality of terms including class terms and series terms, the class terms being defined for all risk classification instruments of a first risk class by the model during the generation of the one or more risk classification instruments, the series terms being defined for the one or more risk classification instruments a given collection of the one or more risk classification instruments at the time of publication of the collection to the networked server, the series terms including an interest spread defining an amount payable to an investor, and a maturity date defining a date on which a principal amount will be returned to the investor where no realization event has occurred.

6. The method of claim 1, wherein a risk classification represents epidemic or pandemic catastrophe risks selected from the group consisting of influenza, respiratory syncytial virus, and bacterial pneumonias that are frequently sequelae of primary viral respiratory infection.

7. The method of claim 1, wherein the one or more risk classification instruments categorize epidemic or pandemic catastrophe risks by a region or by a time frame.

8. The method of claim 1, wherein training the model includes providing input comprising cumulative in-patient charges arising from influenza admissions per 1,000 admissions to a hospital as a function of one or more variables comprising season-to-date's mechanical ventilation procedure rate (ICD-9 procedures 96.7), acute dialysis procedure rate (ICD-9 procedures 54.98 or 38.95), rate of discharge to SNF or LTAC facilities, or in-hospital mortality rate.

9. The method of claim 1, wherein the electronic health record information includes hospital-related information comprising one or more variables for bed-size, teaching status, or geographic location (GIS coordinates).

10. The method of claim 1, wherein the electronic health record information includes region- or community-related information comprising one or more variables for vaccine uptake rate, timing of vaccine availability, or spectrum of vaccine effectiveness against the virus strains that are prevalent in the duration of time.

11. A method of distributing instruments representing securitized epidemic or pandemic catastrophe risk, the method comprising:
  generating a set of transformed data using an expit transformation of structured data accessible via a non-transitory storage medium, the structured data comprising historical insurance claims and associated electronic health record information for a plurality of hospital admissions over an interval of time;
  generating a first risk instrument classifying epidemic or pandemic catastrophe risk using a model trained to predict aggregate risk based on a distribution of the set of transformed data, the first risk instrument being publishable in allotments;
  publishing a first allotment of the first risk instrument to an exchange maintained by a server accessible by multiple users.

12. The method of claim 11, further comprising:
  training the model using Tweedie boosting a first partition of a plurality expit transformed pre-classified historical insurance claims and associated electronic health record information; and
  validating the model using a second partition of the plurality expit transformed pre-classified historical insurance claims and associated electronic health record information.

13. The method of claim 12, wherein the first allotment of the first risk instruments comprise an associated plurality of terms, the plurality of terms including class terms and series terms, the class terms being defined for all risk instruments of a risk class, the series terms being defined for risk instruments of a given allotment at the time of issuance of the allotment, the series terms including an interest spread defining an amount payable to an investor, and a maturity date defining a date on which a principal amount will be returned to the investor if no realization event has occurred.

14. A computer-readable storage device having computer-executable instructions embodied thereon that when executed by a processor, facilitate a method for securitizing epidemic or pandemic catastrophe risk, the method comprising:
  developing a risk classification model using the processor to expit transform a first structured data set retrieved from a remote memory store the training set and train the risk classification model using the expit transformation of the first structured data set, the first structured data comprising pre-classified historical insurance claims and corresponding electronic health record information;
  receiving a second structured data set non-classified historical insurance claims and associated electronic health record information for a plurality of hospital admissions over a duration of time, the second structured data set maintained by a limited access server;
  generating a set of transformed data using one or more processors executing instructions that cause the processors to perform an expit transformation on the received second structured data set;
  generating one or more risk classification instruments using the developed risk classification model to predict aggregate risk based on a distribution of the set of transformed data; and
  publishing a first collection of the one or more risk classification instruments to the server accessible by multiple users.

15. The computer readable storage medium of claim 14, wherein the one or more risk classification instruments include a plurality of risk classes each representing an individual epidemic or pandemic catastrophe risk, and one or more risk classes representing a combination of epidemic or pandemic catastrophe risks represented by two or more of the plurality of risk classes.

16. The computer readable storage medium of claim 15, wherein the individual epidemic or pandemic catastrophe risks are uncorrelated or weakly correlated by time interval or across regions.

17. The computer readable storage medium of claim 14 further comprising causing the first collection of risk instruments to be issued on a first issue date; and causing a second collection of risk instruments of the first risk class to be issued on a second issue date, the second issue date being after the first issue date.

18. The computer readable storage medium of claim 17, wherein the risk classification instruments of the first risk class have an associated plurality of terms, the plurality of terms including class terms and series terms, the class terms being defined for all risk instruments of the first risk class during the establishing of the first risk class, the series terms being defined for risk instruments of a given collection of risk instruments of the first series at the time of issuance of the collection, the series terms including an interest spread defining an amount payable to an investor, and a maturity date defining a date on which a principal amount will be returned to the investor if no realization event has occurred.

19. The computer readable storage medium of claim 15, wherein the risk classes represent epidemic or pandemic catastrophe risks selected from the group comprising in-patient acute-care hospital care, long-term acute care (LTAC), and skilled nursing facility (SNF) care.

20. The computer readable storage medium of claim 15, wherein the risk classes categorize epidemic or pandemic catastrophe risks by a region or by a time period.

* * * * *

UNITED STATES PATENT AND TRADEMARK OFFICE
CERTIFICATE OF CORRECTION

| | | |
|---|---|---|
| PATENT NO. | : 10,671,703 B1 | Page 1 of 1 |
| APPLICATION NO. | : 15/083090 | |
| DATED | : June 2, 2020 | |
| INVENTOR(S) | : Douglas S. McNair | |

It is certified that error appears in the above-identified patent and that said Letters Patent is hereby corrected as shown below:

In the Claims

Column 17, Line 08: After "instruments" please insert --of--.

Column 18, Line 11: Please remove "computer-readable storage device" and replace with --computer readable storage medium--.

Signed and Sealed this
Eleventh Day of August, 2020

Andrei Iancu
*Director of the United States Patent and Trademark Office*